United States Patent
Hall et al.

(10) Patent No.: US 10,890,497 B2
(45) Date of Patent: Jan. 12, 2021

(54) ACTIVE PRESSURE SENSING TOILET GASKET AND METHODS OF USE

(71) Applicants: David R. Hall, Provo, UT (US); K. Jeffrey Campbell, Spanish Fork, UT (US); Andrew Nguyen, Provo, UT (US); Jared Reynolds, Pleasant Grove, UT (US); Joshua Larsen, Spanish Fork, UT (US)

(72) Inventors: David R. Hall, Provo, UT (US); K. Jeffrey Campbell, Spanish Fork, UT (US); Andrew Nguyen, Provo, UT (US); Jared Reynolds, Pleasant Grove, UT (US); Joshua Larsen, Spanish Fork, UT (US)

(73) Assignee: Medic, Inc., Provo, UT (US)

( * ) Notice: Subject to any disclaimer, the term of this patent is extended or adjusted under 35 U.S.C. 154(b) by 211 days.

(21) Appl. No.: 16/045,727

(22) Filed: Jul. 25, 2018

(65) Prior Publication Data
US 2020/0033206 A1 Jan. 30, 2020

(51) Int. Cl.
*G01L 1/08* (2006.01)
*G01L 1/18* (2006.01)
(Continued)

(52) U.S. Cl.
CPC ............. *G01L 1/18* (2013.01); *A61B 5/1102* (2013.01); *A61B 5/1116* (2013.01); *E03D 11/00* (2013.01);
(Continued)

(58) Field of Classification Search
CPC ..... G01L 19/147; G01L 9/0042; G01L 19/04; G01L 9/0054; G01L 9/0072; G01L 13/025; G01L 19/14; G01L 19/0038; G01L 19/0084; G01L 9/0055; G01L 9/0075; G01L 19/0069; G01L 9/0052; G01L 9/0073; G01L 19/0092; G01L 19/0618;
(Continued)

(56) References Cited

U.S. PATENT DOCUMENTS

| 4,503,705 | A | * | 3/1985 | Polchaninoff | G01L 1/20 338/114 |
| 5,033,291 | A | * | 7/1991 | Podoloff | A61B 5/1036 73/172 |

(Continued)

*Primary Examiner* — Andre J Allen

(57) ABSTRACT

The pressure pad which pressure-sensing fabric which is within a gasket and which measures the distribution of pressure on the gasket. Thus, the gasket protects the pressure-sensing fabric from damage due to water or mechanical trauma. The pressure pad includes multiple piezoresistive depositions of piezoresistive depositions ink or paste which act as individual pressure-sensing points. Conductive tracks between the piezoresistive depositions transmit the pressure measurements in the form of electrical signals. The pressure-sensing fabric is connected to a controller and transmits pressure measurements to the controller. Algorithms stored on the controller create a map of absolute mechanical loading to each pressure-sensing point of the pressure pad. The gasket may be mounted beneath a toilet or between plumbing joints. The pressure pad may detect weaknesses in the gasket, a toilet user's weight, a weight of excrement added to the toilet, or a toilet user's posture.

18 Claims, 12 Drawing Sheets

(51) Int. Cl.
*E03D 11/00* (2006.01)
*G01G 19/52* (2006.01)
*A61B 5/11* (2006.01)
*G01G 19/44* (2006.01)

(52) U.S. Cl.
CPC ............ *G01G 19/44* (2013.01); *G01G 19/52* (2013.01); *A61B 2562/0247* (2013.01)

(58) Field of Classification Search
CPC . G01L 19/0645; G01L 19/143; G01L 9/0051; G01L 19/0007; G01L 19/0046; G01L 19/06; G01L 19/0627; G01L 19/0681; G01L 27/002; G01L 9/00; G01L 9/0041; G01L 9/0044; G01L 11/025; G01L 11/04; G01L 19/0023; G01L 19/0672; G01L 19/069; G01L 19/142; G01L 19/145; G01L 19/16; G01L 7/00; G01L 9/0047; G01L 9/06; G01L 9/065; G01L 9/12; G01L 11/02; G01L 13/00; G01L 15/00; G01L 19/0015; G01L 19/003; G01L 19/02; G01L 19/0609; G01L 19/083; G01L 19/10; G01L 19/148; G01L 27/005; G01L 7/08; G01L 7/082; G01L 7/163; G01L 7/166; G01L 9/0045; G01L 9/0048; G01L 9/006; G01L 9/007; G01L 9/0076; G01L 9/04; G01L 9/045; G01L 9/125; G01L 11/00; G01L 17/00; G01L 19/00; G01L 19/0076; G01L 19/08; G01L 19/141; G01L 19/146; G01L 1/142; G01L 1/2262; G01L 1/246; G01L 21/12; G01L 23/16; G01L 27/007; G01L 7/04; G01L 7/063; G01L 7/084; G01L 7/086; G01L 7/16; G01L 9/0002; G01L 9/0007; G01L 9/0016; G01L 9/0019; G01L 9/0022; G01L 9/0027; G01L 9/0033; G01L 9/0039; G01L 9/005; G01L 9/0058; G01L 9/0077; G01L 9/0079; G01L 9/008; G01L 9/0092; G01L 9/0095; G01L 9/025; G01L 9/08; G01L 9/085; G01L 9/105; G01L 9/14; G01L 9/16; A61B 5/1036; A61B 5/1038; A61B 2562/0247; A61B 5/6807; A61B 2562/046; A61B 5/112; A61B 5/4528; A61B 5/6892; A61B 5/0816; A61B 5/447; A61B 5/0002; A61B 5/0205; A61B 5/103; A61B 5/11; A61B 5/1126; A61B 5/113; A61B 2560/0214; A61B 5/02055; A61B 5/024; A61B 5/4818; A61B 5/0031; A61B 5/076; A61B 5/1116; A61B 5/1118; A61B 2034/102; A61B 2090/064; A61B 2562/02; A61B 2562/0219; A61B 2562/166; A61B 5/02438; A61B 5/1071; A61B 5/1074; A61B 5/1112; A61B 5/1117; A61B 5/1121; A61B 5/1123; A61B 5/224; A61B 5/4504; A61B 5/4533; A61B 5/486; A61B 5/6811; A61B 5/6812; A61B 5/6829; A61B 5/7242; A61B 5/742; A61B 10/00; A61B 2017/564; A61B 2034/105; A61B 2034/2055; A61B 2090/3983; A61B 2503/04; A61B 2503/08; A61B 2503/10; A61B 2503/40; A61B 2505/00; A61B 2505/09; A61B 2560/0242; A61B 2560/0285; A61B 2560/0412; A61B 2560/0456; A61B 2560/0468; A61B 2560/0475; A61B 2562/0252; A61B 2562/0266; A61B 2562/0271; A61B 2562/0276; A61B 2562/12; A61B 34/10; A61B 34/20; A61B 5/0015; A61B 5/0022; A61B 5/0053; A61B 5/0064; A61B 5/015; A61B 5/021; A61B 5/02444; A61B 5/031; A61B 5/04; A61B 5/055; A61B 5/107; A61B 5/1076; A61B 5/1077; A61B 5/1102; A61B 5/1113; A61B 5/1114; A61B 5/1115; A61B 5/1122; A61B 5/1124; A61B 5/1127; A61B 5/14532; A61B 5/14542; A61B 5/22; A61B 5/4023; A61B 5/412; A61B 5/442; A61B 5/45; A61B 5/4519; A61B 5/4523; A61B 5/4824; A61B 5/4833; A61B 5/4842; A61B 5/4848; A61B 5/4851; A61B 5/4866; A61B 5/6803; A61B 5/6806; A61B 5/681; A61B 5/6831; A61B 5/6833; A61B 5/6843; A61B 5/6846; A61B 5/6887; A61B 5/6891; A61B 5/6893; A61B 5/6895; A61B 5/6898; A61B 5/721; A61B 5/7225; A61B 5/7246; A61B 5/7264; A61B 5/7275; A61B 5/7405; A61B 5/743; A61B 5/7455; A61B 6/03; A61B 6/0407; A61B 90/36; A61B 90/361; A43B 3/0005; A43B 7/00; A43B 13/14; A43B 17/006; A43B 23/0235; A43B 23/0275; A43B 3/00; A43B 5/001; A43B 13/38; A43B 13/386; A43B 17/00; A43B 3/001; A43B 5/00; A43B 7/141; A43B 7/142; A43B 7/144; A43B 7/1445; A43B 11/00; A43B 17/02; A43B 1/0054; A43B 3/0015; A43B 7/1455; A43B 7/147
USPC .............................................. 73/172, 700–756
See application file for complete search history.

(56) References Cited

U.S. PATENT DOCUMENTS

| | | | | |
|---|---|---|---|---|
| 5,941,835 | A * | 8/1999 | Sundman | ............ A61B 5/1036 600/592 |
| 10,546,664 | B2 * | 1/2020 | Yonekura | ................ C08K 3/30 |
| 2008/0135310 | A1 * | 6/2008 | Pomposo Alonso | ... G06F 3/045 178/18.05 |
| 2015/0331533 | A1 * | 11/2015 | McMillen | ............ A61B 5/6843 345/174 |
| 2017/0354372 | A1 * | 12/2017 | Varadan | ................ A61B 5/0408 |
| 2019/0003907 | A1 * | 1/2019 | Dervish | ................ A61B 5/6807 |

* cited by examiner

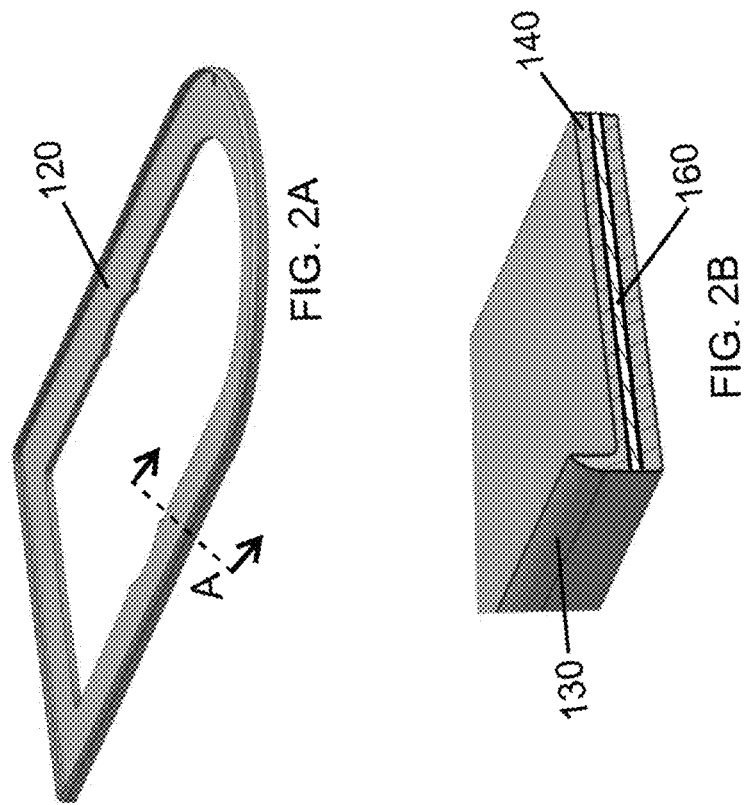
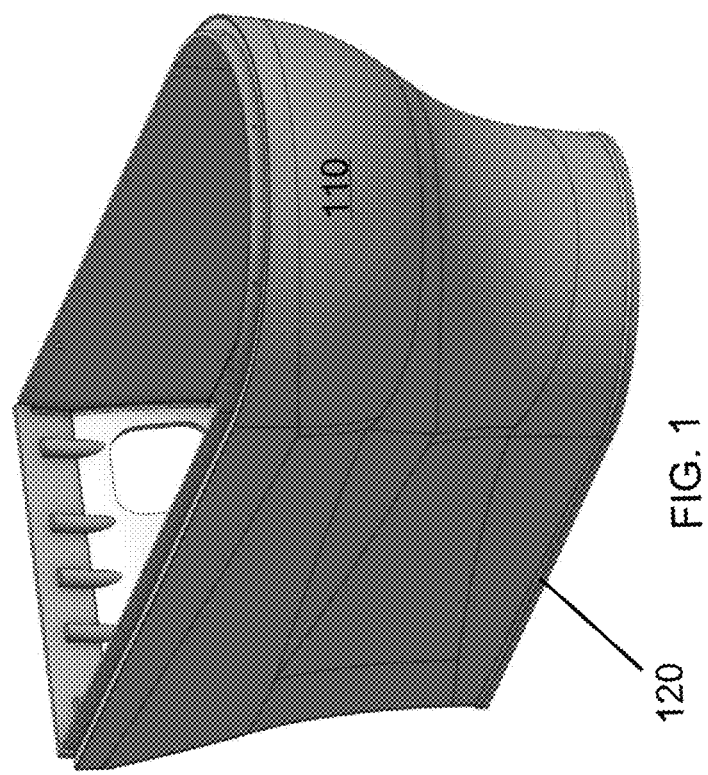

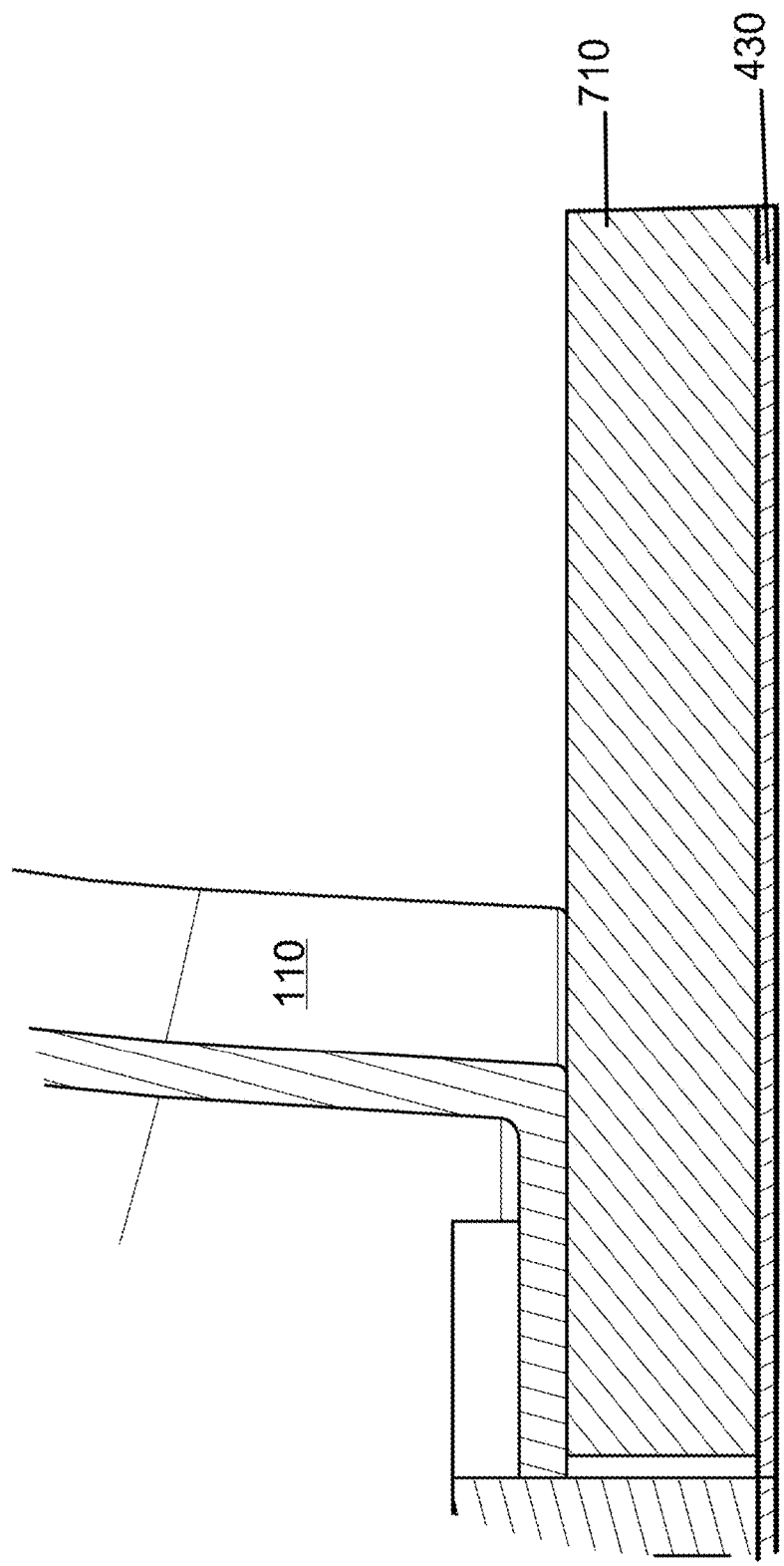

ACTIVE PRESSURE SENSING TOILET GASKET AND METHODS OF USE

BACKGROUND

Field of the Invention

This disclosure relates to gaskets, specifically on toilets, and pressure measurement devices.

Background of the Invention

The amount of mechanical load that is transferred between two mechanical surfaces is often a useful measurement but also one that is difficult to ascertain accurately. Furthermore, often a measurement of load distribution across a surface is needed, rather than a measurement of total load. For example, in a gasket which acts as a water-resistant seal at the base of a toilet or between joints in plumbing, a single part of the gasket may fail causing a leak. A total load measurement may not show a significant change due to the weak section of the gasket. In contrast, a measurement of load distribution around the gasket would identify a weak area in the seal.

Existing active gasket technologies do not, with one device, measure the distribution of load around the entire circumference of the seal. Current technology includes load measurement devices using capacitive sensors in gaskets. However, these devices use monolithic capacitor plates rather than distributed sensors. They instead provide an average load. Consequently, existing gaskets do not pinpoint the location of future possible leaks based on uneven load distributions.

In addition to detecting leaks, an accurate measurement of distributed load on a toilet would be useful to collect data related to a user's health status. A user's body weight, posture or position on the toilet seat, and weight of deposited excrement could be used by a healthcare provider to assess the user's health.

BRIEF SUMMARY OF THE INVENTION

We disclose a device which includes a pressure pad which collects pressure distribution measurements. The pressure pad does not simply collect an overall pressure or weight measurement. Rather, it measures the distribution of pressure throughout a pressure pad.

The pressure pad includes a gasket constructed from one or more water-resistant compressible materials. A pressure-sensing fabric is in mechanical connection with the gasket. The pressure-sensing fabric may be as described in U.S. Pat. No. 9,032,804. In some embodiments, the pressure-sensing fabric may be sandwiched between a top and a bottom layer of the gasket. The pressure-sensing fabric is thereby protected from water or mechanical damage.

The pressure pad may have a footprint that is the same or similar to the footprint of a toilet base under which the pressure pad may be mounted. Some embodiments may also include an external pressure sensor, which may be a strain gauge or a foot pad which is an extension of the pressure pad beneath the toilet base. The foot pad and the pressure pad to be placed beneath the toilet base may include multiple pressure-sensing zones which independently collect pressure distribution data. Alternatively, the pressure pad and foot pad may be one continuous pressure-sensing zone. In other embodiments, the pressure pad may be disposed between plumbing joints.

The pressure-sensing fabric may be in connection with a controller. The controller may store an algorithm which creates a pressure distribution map using data collected by the pressure-sensing fabric. The algorithms may be configured to measure a weight of water in an unused toilet system, a weight of excrement added to the toilet during a toilet session, and a total weight of water used during a toilet session. The algorithms may also be configured to measure the body weight of a user, with or without an external pressure sensor. The algorithms may further be configured to analyze a user's posture and to analyze ballistic heart measurements taken by the device. Methods of use of the disclosed device include methods of collecting these measurements.

In some embodiments, the device may be mounted beneath a medical toilet. The medical toilet may include devices and sensors, in addition to the pressure pad, which collect data from a user which may be relevant to the user's health status. These devices and sensors may include, but are not limited to, a spectrometer which may perform an analysis of the user's urine or feces, a stethoscope, a blood pressure analyzer, an electrocardiogram analysis device, and devices which collect bioimpedance measurements. Methods of using the disclosed device include collecting measurements from the device and the medical toilet for use in assessing the health status of a user.

In embodiments in which the pressure pad is mounted beneath a toilet, the pressure pad may be placed either on or beneath the floor. In embodiments in which the pressure pad is on the floor, the pressure pad is at an elevation that is above the floor level. In embodiments in which the pressure pad is beneath the floor, a layer of flooring may be positioned on top of the pressure pad at the same level as the remainder of the flooring in the room. In this embodiment, the pressure pad is beneath the floor so there is nothing for a user to trip on. A compressible pad may be placed above or below the pressure pad in these embodiments and may be constructed of carpet padding.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings.

FIG. 1 illustrates a perspective view of a toilet base mounted on a pressure pad according to an embodiment of the disclosure.

FIG. 2A illustrates a perspective view of a pressure pad according to an embodiment of the disclosure.

FIG. 2B illustrates a cross-sectional view of the pressure pad of FIG. 2A.

FIG. 7B a cross section of an embodiment of the pressure pad mounted beneath a toilet and below the floor.

DETAILED DESCRIPTION OF THE INVENTION

Figure 3:
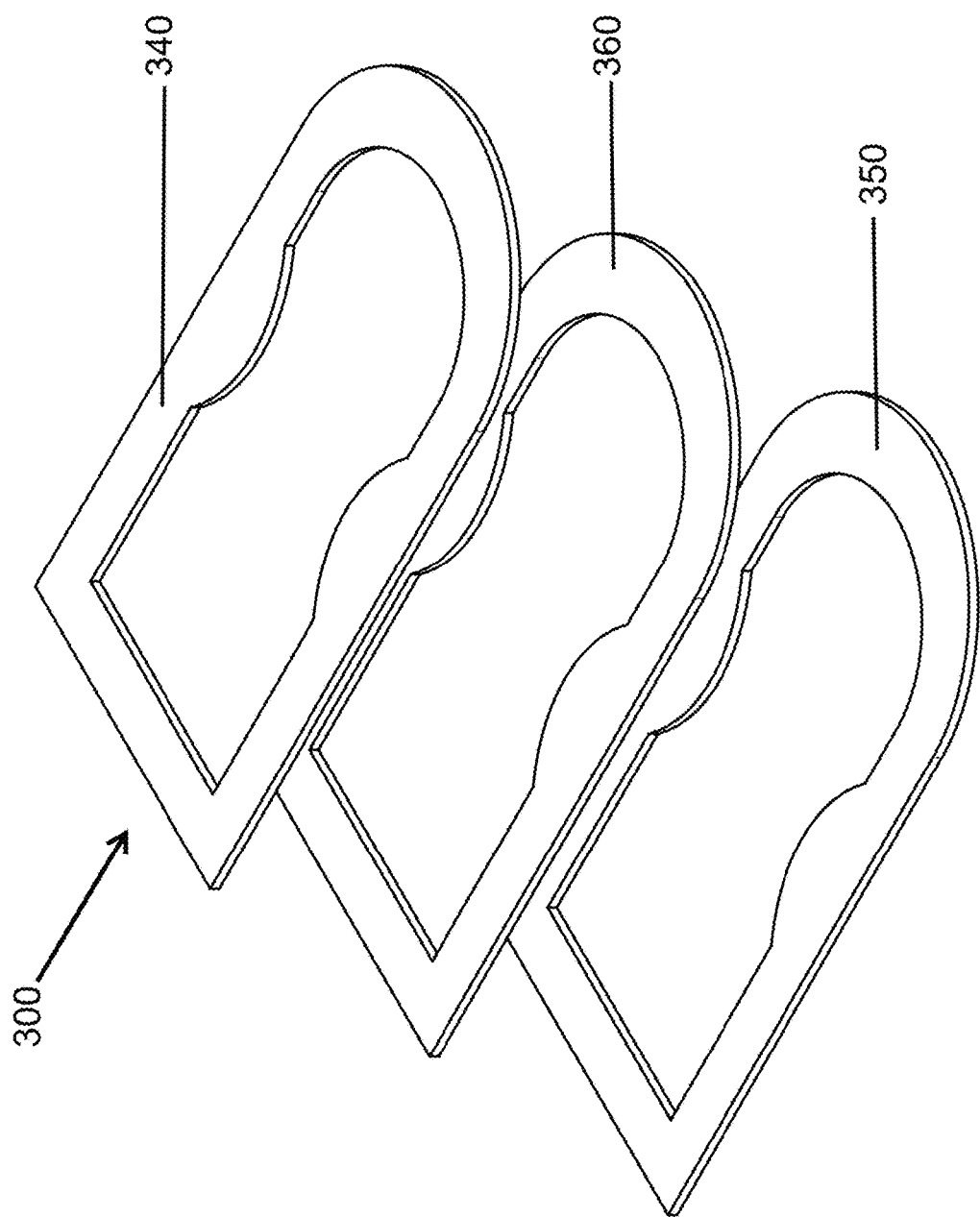
FIG. 3 illustrates an exploded view of a pressure pad according to an embodiment of the disclosure.

Definitions:

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "electronic" means either wired or wireless. For example, the phase "in electronic communication" means either a wired communication between two devices or could mean a wireless communication between devices, such as Wi-Fi.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a device and method of using the device to measure the distribution of weight load on a toilet using a water-resistant pressure pad. The device is a pressure pad which includes a gasket and a pressure-sensing fabric. The gasket may be constructed from one or more water-resistant compressible materials. The pressure-sensing fabric may be as described in U.S. Pat. No. 9,032,804, titled "Large-area extensible pressure sensor for textiles surfaces," filed on Jul. 3, 2013, which is hereby incorporate by reference in its entirety.

The pressure-sensing fabric may include a support which is flexible, extensible, and elastic. An extensible and elastic conductive ink or paste may be printed on the support or substrate using any printing technique known in the art. The conductive ink or paste may be printed to form multiple primary tracks which transmit a printed electrical signal. Multiple piezoresistive depositions may be disposed on the primary tracks. In some embodiments, the piezoresistive depositions are printed onto the primary tracks. In some embodiments, the piezoresistive depositions may be covered with a conductive deposition in the same form as the piezoresistive depositions and may be in contact with the secondary tracks. These piezoresistive depositions act as pressure-sensing points on the pressure pad. Consequently, the pressure pad may give in response to pressure along with the compressible material which forms the gasket. Each of the piezoresistive depositions may be linked to a secondary track. The secondary tracks may also comprise an extensible and elastic conductive ink or paste and be printed using any printing technique known in the art.

In some embodiments, the piezoresistive depositions may be circular as shown in U.S. Pat. No. 9,032,804. In some embodiments, the piezoresistive depositions may be rectangular shaped, including square. The piezoresistive depositions may be positioned directly next to each other, spaced equal to or less than 5 mm apart, or overlapping so that there is no "dead space" between them where no measurement is taken. In an embodiment, the piezoresistive depositions are square and positioned directly next to each other.

In some embodiments, the gasket comprises a layer of water-resistant, compressible material which is adjacent to the pressure-sensing fabric. In some embodiments, the gasket includes a top layer and a bottom layer, each constructed of water-resistant compressible material. The pressure-sensing fabric may be sandwiched between the top and bottom layers. In this embodiment, the top and bottom layers of the gasket protect the pressure-sensing fabric from damage due to water or mechanical force. In other embodiments, the pressure pad is embedded within the material from which the gasket is constructed. This design may be accomplished by molding the material, for example, a rubber-like material, around the pressure-sensing fabric.

The pressure pad may be in electronic connection with a controller. Both the primary tracks and the secondary tracks may be connected to a controller without crossing each other. The controller may include a memory and non-transitory computer-readable medium which stores algorithms comprising instructions for processing the weight distribution data the pressure pad collects. The algorithms may compile a distribution of weight load on the gasket, thereby creating a pressure map.

In some embodiments, the pressure pad has a footprint which is similar to the footprint of a toilet base beneath which the pressure pad may be mounted. The pressure pad may include two arms which are approximately the length of the sides of the toilet base. The two arms may be connected to each other by a front lateral extension and a rear lateral extension. The front lateral extension may connect the two arms at their front ends and the rear lateral extension may connect the two arms at the rear of the two arms. Thus, the two arms and the front and rear lateral extensions define at least part of the footprint of the pressure pad and the footprint of the toilet base. They may also define an orifice within the pressure pad. The orifice may be an open space in the pressure pad through which a toilet flange, mounting brackets which may secure the toilet to the floor, and plumbing may pass.

In some embodiments the gasket may extend beyond the pressure-sensing fabric, at least on an inner edge of the two arms and the front and rear lateral extensions. Consequently, the inner perimeter defining the orifice may include a region that includes the gasket but no pressure-sensing fabric. This region may house wires which are in electronic communication with the pressure-sensing fabric.

An edge of the two arms and the front and rear lateral extensions may include a lip. The lip may be disposed on the inner or outer edges of the two arms and the front and rear lateral extensions. The lip may extend upward or downward. This lip may assist the gasket in preventing water, which has leaked from the plumbing associated with the toilet, from damaging the floor or the pressure-sensing fabric.

The pressure map may include a charging circuit which may be configured to perform wireless charging. In some embodiments, the antenna within the charging circuit may be curved to match a profile of the toilet base and elongated to match the points of contact for the pressure pad and the toilet.

In some embodiments, the pressure pad may be connected to an external pressure sensor. The external pressure sensor may comprise a strain gauge, for example, a standard bathroom scale, positioned in front of the toilet. The foot pad may be an extension of the pressure pad beneath the toilet base. In either example, the external pressure sensor may be placed in front of the toilet where a seated user would place his or her feet and be in electronic connection with the controller. The external pressure sensor may collect a weight measurement or a distribution of weight load measurement which the algorithm on the controller may add to the distribution of weight load measurement the pressure pad collects from the pressure applied to the toilet. This may result in a more accurate assessment of the user's total body weight and other assessments related to the user's physical status.

In some embodiments, the pressure pad includes a plurality of independent pressure-sensing zones. In these embodiments, each of pressure-sensing zones reports a pressure distribution to the controller independently of each other.

In some embodiments, the pressure pad is mounted below a toilet base which is positioned below a toilet seat. When installed, the base may be in contact with the floor. A water-resistant gasket is in mechanical contact with the perimeter of the base. The gasket creates a seal which prevents water leakage through the base caused by defective plumbing in the toilet.

In other embodiments, the pressure pad is positioned between two joints of pipe, for example, plumbing pipe. The distribution of pressure measurements may be used to identify a region of the gasket which is weakened and in danger of failing. This information may prevent plumbing fails and the inevitable water damage to follow.

A method of using the device includes the step of collecting multiple data points, each measured by one of the piezoresistive depositions, using the pressure pad. Each of the multiple data points represents a pressure point on the gasket. The multiple data points may be transmitted to the controller and stored on the memory of the controller. The data may be processed immediately using algorithms stored on the controller or used to perform calculations at a later time. The device may also include a data transmission port.

The method may include the step of transmitting the distribution of weight load on the pressure pad to an external database through the data transmission port.

The algorithms stored on the controller may construct a distribution of weight load on the gasket (hereinafter, "pressure map") which may be used in one of multiple ways. In one embodiment, the algorithms stored on the controller may use the pressure map to identify an irregularity in the weight distribution which may be associated with a weak region in the gasket.

This uneven load distribution may indicate that the seal the gasket forms has or will soon be breached. In some embodiments, the controller may be in electronic communication with a user interface (hereinafter, "UI"). A user may interact with the UI through an external device including, but not limited to, a computer or mobile device. A signal may be viewed through the UI providing a warning that the gasket has a weakened area which may result in a water leak. In some embodiments, the UI may simply be a light, a series of lights, or a screen on the toilet. For example, the toilet may have a series of lights in the shape of the gasket on it. One or more lights associated with the region of the gasket that has been weakened may become illuminated informing the user both that the gasket is compromised and where o the gasket the weakened area has been detected.

The controller may also apply algorithms stored thereon which calculate a weight of water in an unused toilet system, a weight of excrement added to the toilet during a toilet session, and a total weight of water used during a toilet session. In an example, the pressure pad may perform measurements before a user has approached the toilet and the algorithm may use this measurement to determine the weight of water in the toilet system. The user may then approach the toilet and deposit excrement into the toilet bowl. The pressure pad may perform a subsequent measurement and the algorithm may use this data to calculate the weight of the added excrement. The user may then flush the toilet and the pressure pad may conduct weight distribution measurements during the flush. The difference between the initial weight load and the lowest weight load during the flush may be used to calculate the amount of water used during the toilet session.

The controller may also apply algorithms stored thereon which calculate a user's body weight. The toilet may store a baseline weight distribution measurement which was performed before a user approached the toilet. The user may then sit on the toilet seat and the pressure pad may collect a weight distribution measurement. The controller may use the difference in the weight distribution measurement before and during the time the user is seated on the toilet to calculate the user's body weight.

The algorithm which measures a user's body weight may also calculate the user's body weight before and after a toilet session. The pressure pad may perform weight distribution measurements and the algorithm may calculate the user's body weight as the user sits on the toilet as described above. The user may deposit bodily waste into the toilet and flush the toilet. The pressure pad may perform a second weight distribution measurement and the algorithm may perform a calculation after the flush while the user is still seated on the toilet. Alternatively, the user may leave the toilet and the pressure pads may measure the added weight of the excrement prior to flushing the toilet. The algorithm may subtract the weight of the excrement from the body weight of the user which was measured before the excretion event to determine the body weight of the user after a toilet session.

In some embodiments, the controller may store algorithms which calculate a postural assessment of a user seated on the toilet. The pressure pad may conduct measurements and the controller may compile a pressure map of the user seated on the toilet. Irregularities in the weight distribution may indicate an asymmetric posture. The algorithm may identify muscular or skeletal pathologies based on the user's posture.

In some embodiments, the method may use the toilet to perform ballistic heart measurements. In an example, the user may be seated on the toilet while the pressure pad collects multiple pressure distribution measurements. As the user's heart beats, blood is rapidly forced from the heart into the blood vessels causing a momentary change in the pressure applied to the toilet seat through the user's thighs. The pressure pad may detect these changes in pressure. Each of the multiple pressure distribution measurements may represent a data set which may be transmitted to the controller. An algorithm stored on the controller may calculate ballistic heart measurements using the multiple data sets. In some embodiments, the ballistic heart measurements may be stored in the memory of the controller for later analysis or comparison to other measurements.

In some embodiments, the toilet may be a medical toilet which includes one or more sensors, in addition to the pressure pad, which collect data from a user which may be relevant to the user's health status. In an example, the medical toilet may include a spectrometer which may perform an analysis of the user's urine or feces. The toilet may include a stethoscope which may measure a user's heart rate, cardiac rhythm, and breathing rate. In an example, the toilet may be that disclosed in U.S. patent application Ser. No. 15/215,008 filed on Jul. 20, 2018 which is hereby incorporated by reference in its entirety. The toilet may detect a user's blood pressure or collect electrocardiogram measurements. The toilet may collect bioimpedance measurements through sensors on the toilet seat or through handles connected to the toilet.

In some embodiments, the controller may include a data transmission port. The data transmission port may transmit weight distribution measurements, pressure maps, and calculations the algorithms stored on the controller have performed to a remote, external controller or database. In embodiments which include a medical toilet, the measurements collected by the medical toilet in addition to those related to the pressure pad may also be transmitted to the remote, external controller or database. In this embodiment, a healthcare provider may access the transmitted data to perform an assessment of the user's health status.

Referring now to the drawings, FIG. 1 illustrates a toilet base 110 which may be part of a toilet according to the disclosure. Pressure pad 120 is in contact with the bottom perimeter of toilet base 110. Pressure pad 120 provides a water tight seal around toilet base 110 to prevent water damage due to plumbing leaks while also collecting a weight distribution measurement.

FIG. 2A illustrates pressure pad 120 of FIG. 1 separated from toilet base 110. Pressure pad 120 is designed to be in contact with the entire bottom perimeter of toilet base 110 when mounted. Consequently, a weight load applied to the toilet through toilet base 110 will be transmitted to pressure pad 120. However, the weight load may not be evenly distributed as when a section of the gasket within pressure pad 120 is compromised or a user sits, perhaps unevenly, on the toilet.

FIG. 2B is a cross-sectional view of pressure pad 120 of FIG. 2A. The section is taken across the plane labeled "A" in FIG. 2A. Pressure pad 120 includes a gasket which includes top layer 140 and bottom layer 150, both constructed of a water-resistant, compressible material. The gasket further includes lip 130 which extends upward into the hollow region of the toilet base and is placed adjacent to the inner perimeter of the bottom edge of the toilet base when pressure pad 120 is mounted. This creates a water-resistant seal between the toilet base and the floor and between the plumbing and the toilet base along the floor. Pressure-sensing fabric 160 is sandwiched between top layer 140 and bottom layer 150 and is protected from water damage and mechanical impact by the two layers of the gasket.

FIG. 3 illustrates an exploded view of pressure pad 300 according to an embodiment of the disclosure. Pressure pad 300 includes a water-resistant, compressible gasket which includes top layer 340 and bottom layer 350. Pressure-sensing fabric 360 is sandwiched between top layer 340 and bottom layer 350. The two layers protect pressure-sensing fabric 360. Therefore, unlike most gaskets with active elements, pressure pad 300 may be practical for long-term installation without frequent replacement. Pressure-sensing points throughout pressure-sensing fabric 360 detect a local weight load at each point on pressure pad 300. In an example, if a user were seated unevenly on a toilet which is mounted on pressure pad 300, the pressure-sensing points throughout pressure-sensing fabric 360 would detect the uneven weight load. A controller in electronic connection with pressure-sensing fabric 360 would compile a pressure map identifying the uneven weight load on pressure pad 300.

Figure 4A:
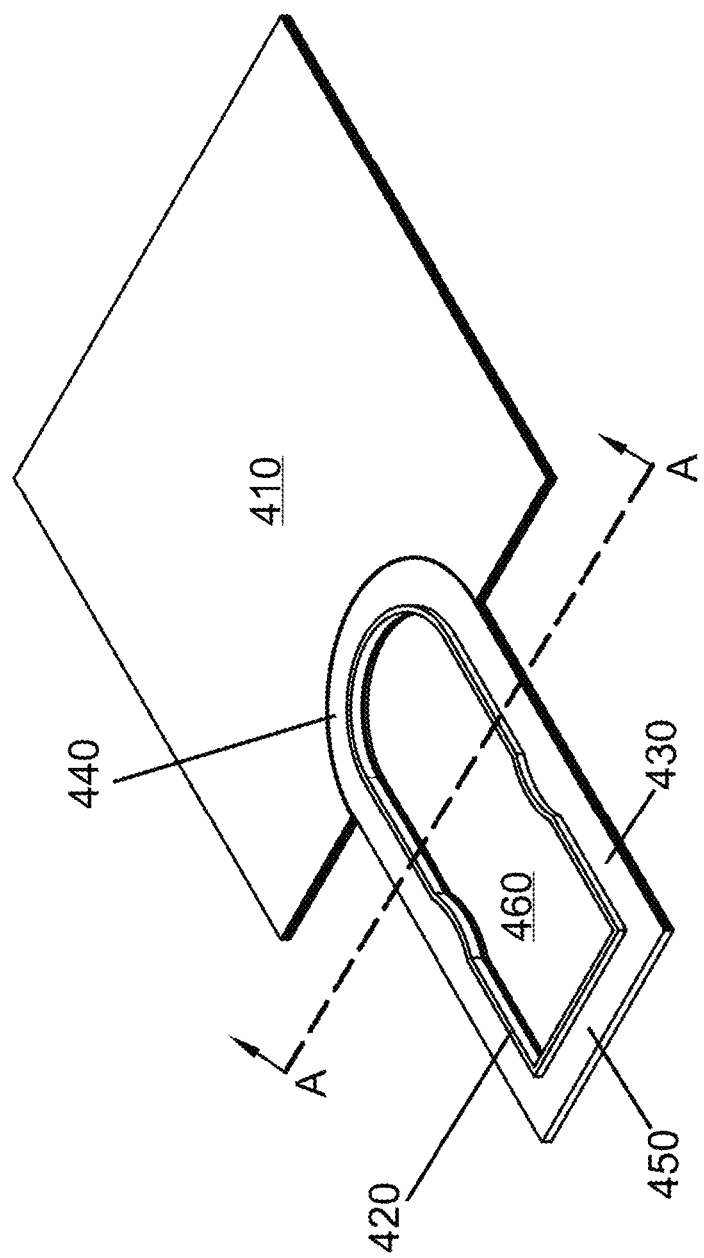
FIG. 4A illustrates a top view of a pressure pad according to an embodiment of the disclosure.

FIG. 4A illustrates a top view of an embodiment the disclosed pressure pad. Pressure pad 400 includes foot pad 410 where a user may rest his or her feet while seated on the toilet. Foot pad 410 may collect the weight of the user's feet and legs which may be added to weight measured through the part of pressure pad 400 which is placed beneath the base of a toilet. Arm 420 and arm 430 extend from foot pad 410, underneath the sides of the base of a toilet and along its perimeter. Pressure pad 400 includes front lateral extension 440 and rear lateral extension 450 which connect arms 420 and 430 at their front and rear ends respectively. Accordingly, arms 420 and 430 and front lateral extension 440 and rear lateral extension 450 may be placed beneath the perimeter of the base of the toilet. When pressure pad 400 is mounted, foot pad 410 extends in front of the toilet. Orifice 460 is defined by arms 420 and 430, front lateral extension 440, and rear lateral extension 450 and may be the dimensions of the footprint of the base of the toilet. Orifice 460 provides an opening through which plumbing extending from the toilet and connecting to a sewer pipe may pass.

Figure 4B:
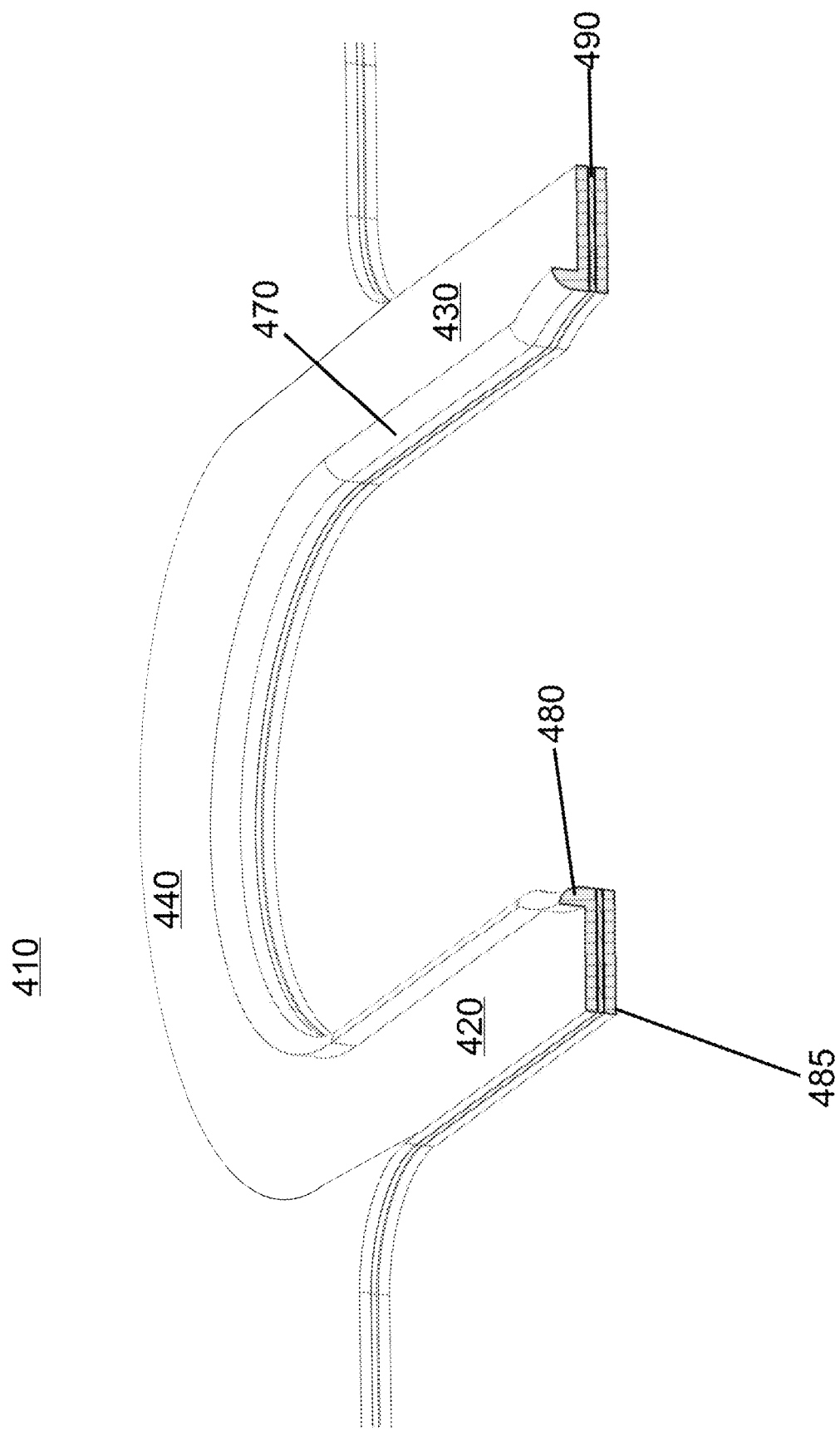
FIG. 4B illustrates a cross-sectional view of the pressure pad of FIG. 4A.

FIG. 4B illustrates a cross-sectional view of pressure pad 400 shown in FIG. 4A. The section is taken from the plane marked "A" in FIG. 4A. Similar to the embodiment shown in FIG. 2B, pressure pad 400 includes a gasket with lip 470 around orifice 460. The gasket also includes top layer 480 and bottom layer 485, both which may be constructed from a water-resistant, compressible material. Pressure-sensing fabric 490 is disposed between top layer 480 and bottom layer 485.

Figure 5:
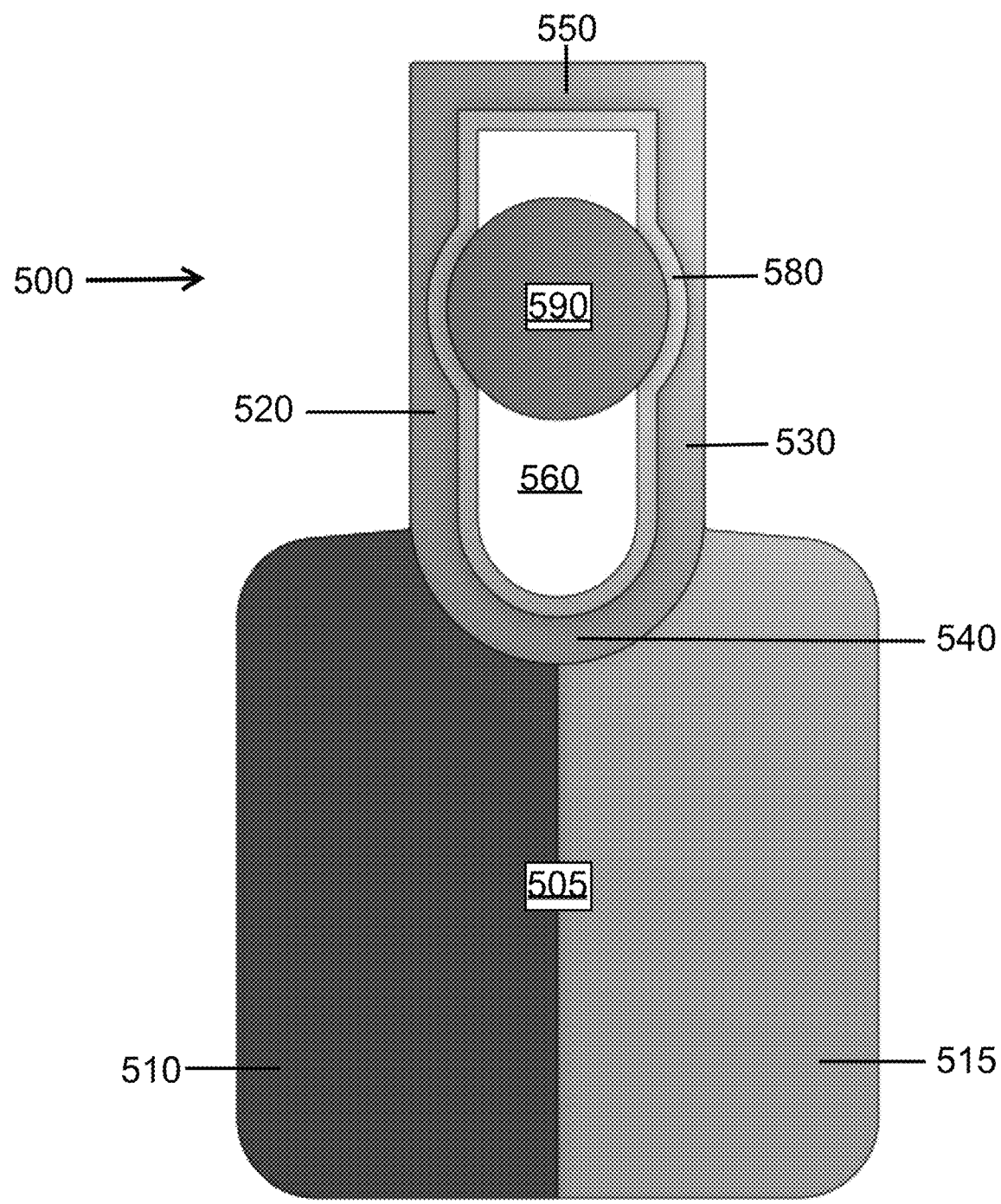
FIG. 5 illustrates a schematic top view of an embodiment of a pressure pad with multiple pressure-sensing zones according to an embodiment of the disclosure.

FIG. 5 illustrates a schematic top view of pressure pad 500, which is an embodiment of the disclosed pressure pad. Pressure pad 500 includes foot pad 505 which is divided into two individual pressure-sensing zones, zone 510 and 515. A third pressure-sensing zone extends from the foot pad toward the toilet and includes arms 520 and 530, which are similar to arms 420 and 430 of the embodiment shown in FIG. 4A. Arms 520 and 530 may extend beneath the lateral perimeter of a toilet when pressure pad 500 is mounted. The third pressure-sensing zone also includes front lateral extension 540, and rear lateral extension 550 which are similar to front lateral extension 440, and rear lateral extension 450 shown in FIG. 4A. Each of zones 520, 530, and the third pressure-sensing zone include separate sections of the pressure-sensing fabric described herein and may each detect pressure independently of each other. Each of zones 520, 530, and the third pressure-sensing zone also include the water-resistant, compressible layer of the gasket above and below the pressure-sensing fabric as illustrated in FIG. 3 (top layer and bottom layer). Gasket edge 580 is an edge of pressure pad 500 which includes the water-resistant, compressible layers of the gasket but does not include pressure-sensing fabric. In some embodiments, gasket edge 580 includes a lip as shown in FIG. 2B (see lip 130). Gasket edge 580 includes available space to run wires and/or leads to zones 520, 530, and the third pressure-sensing zone within pressure pad 500. Orifice 590 is a "Keep Out" area through which the toilet flange may extend. Orifice 590 is not available for pressure-sensing fabric nor wiring. Rather, plumbing which connects the toilet to sewer pipes may extend through orifice 590. Mounting brackets which secure the toilet to the floor may also be placed within orifice 590.

Figure 6:
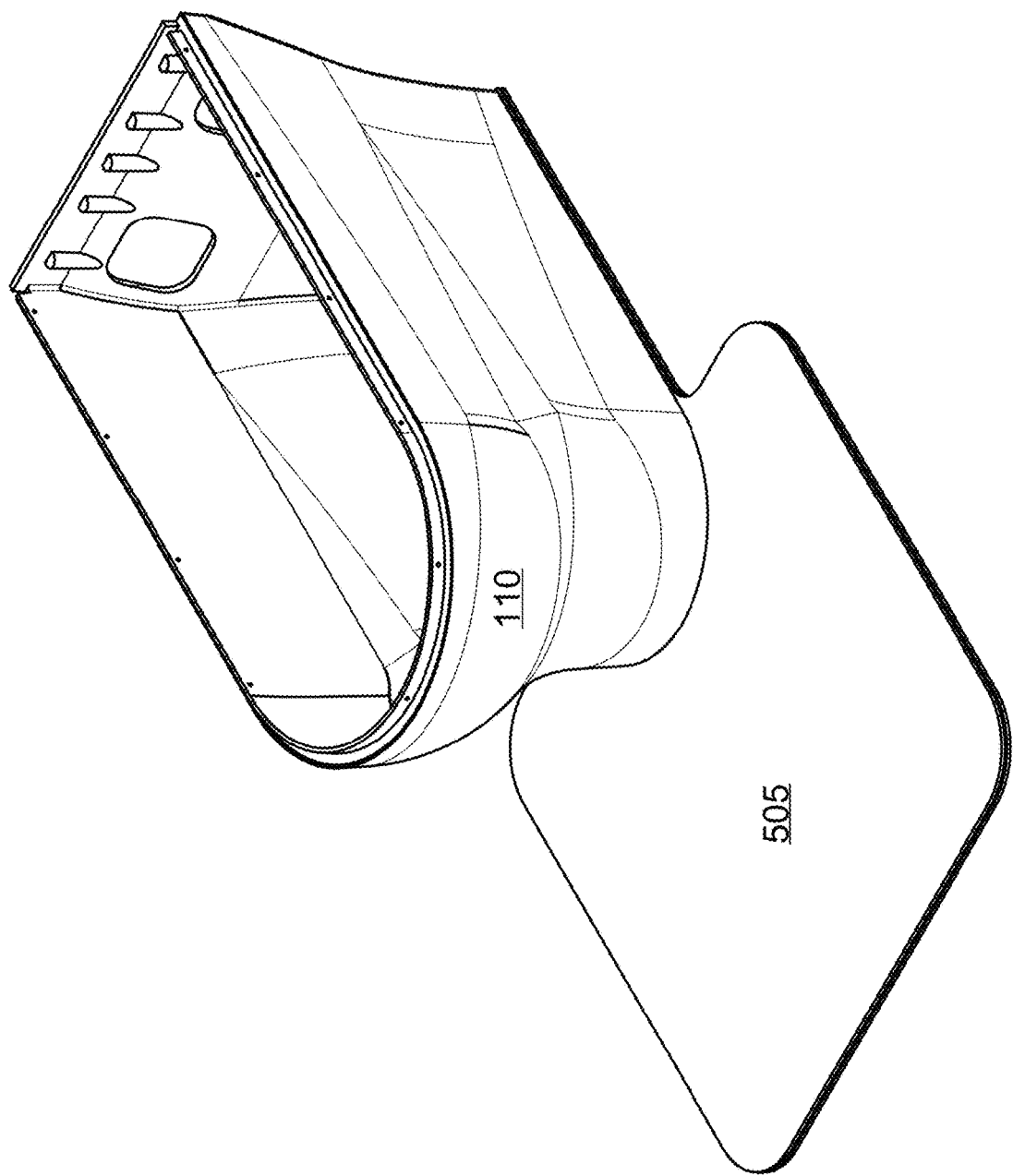
FIG. 6 illustrates a perspective view of a pressure pad with a toilet mounted thereon according to an embodiment of the disclosure.

FIG. 6 illustrates pressure pad 500, first shown in FIG. 5, mounted beneath toilet base 110. Arms 520 and 530, front lateral extension 540, and rear lateral extension 550 are placed underneath the perimeter of toilet base 110. Front lateral extension 540 is shaped to accommodate the rounded shape of the front of toilet base 110. These four components comprise the third pressure-sensing zone discussed with regard to FIG. 5. The third pressure-sensing zone extends underneath the perimeter of toilet base 110 so that pressure pad 500 senses the weight distribution on toilet base 110. Foot pad 505 extends in front of toilet base 110. A user seated on a toilet which includes toilet base 110 may place his or her feet on foot pad 505 which may collect a weight distribution including the weight of the user's feet and legs.

Figure 7A:
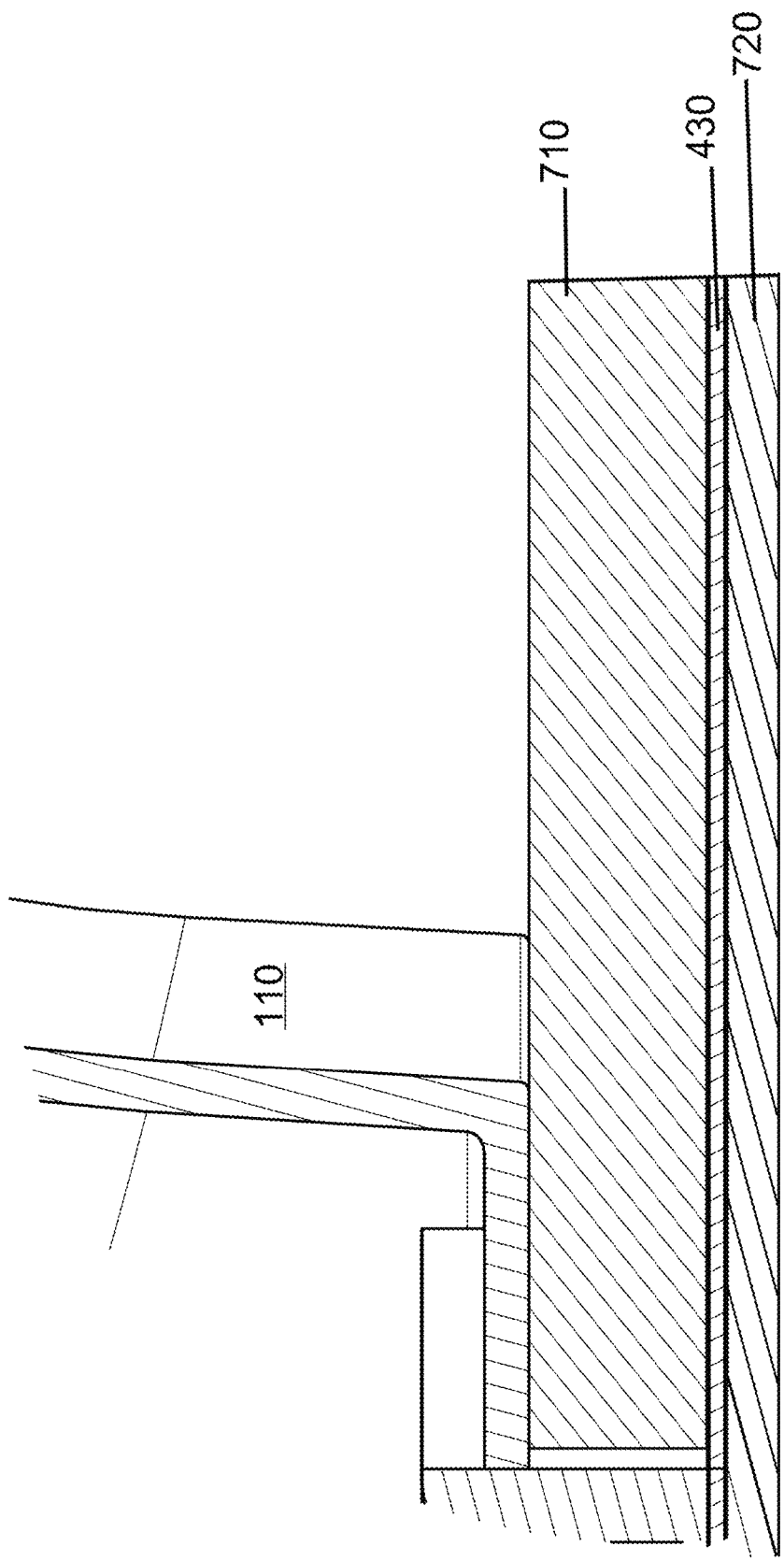
FIG. 7A illustrates a cross-section of an embodiment of the pressure pad mounted beneath a toilet, below the floor, and on top of a compressible pad.

FIGS. 7A and 7B illustrate embodiments of the pressure pad mounted below a toilet in which the pressure pad is below the floor level. Both FIGS. 7A and 7B show pressure pad 420 below floor 710. Toilet base 110 is installed into floor 710 with pressure pad 420 extending beneath toilet base 110. The embodiment of FIG. 7A includes compressible pad 720 beneath pressure pad 420. In some embodiments, compressible pad 720 may be a carpet pad. In both the embodiments of FIGS. 7A and 7B, the pressure pad is below the level of the floor to prevent the user from tripping on the pressure pad. In fact, the user may not even notice the presence of the pressure pad and may use the toilet without attention to the measurements the pressure pad conducts.

Figure 8:
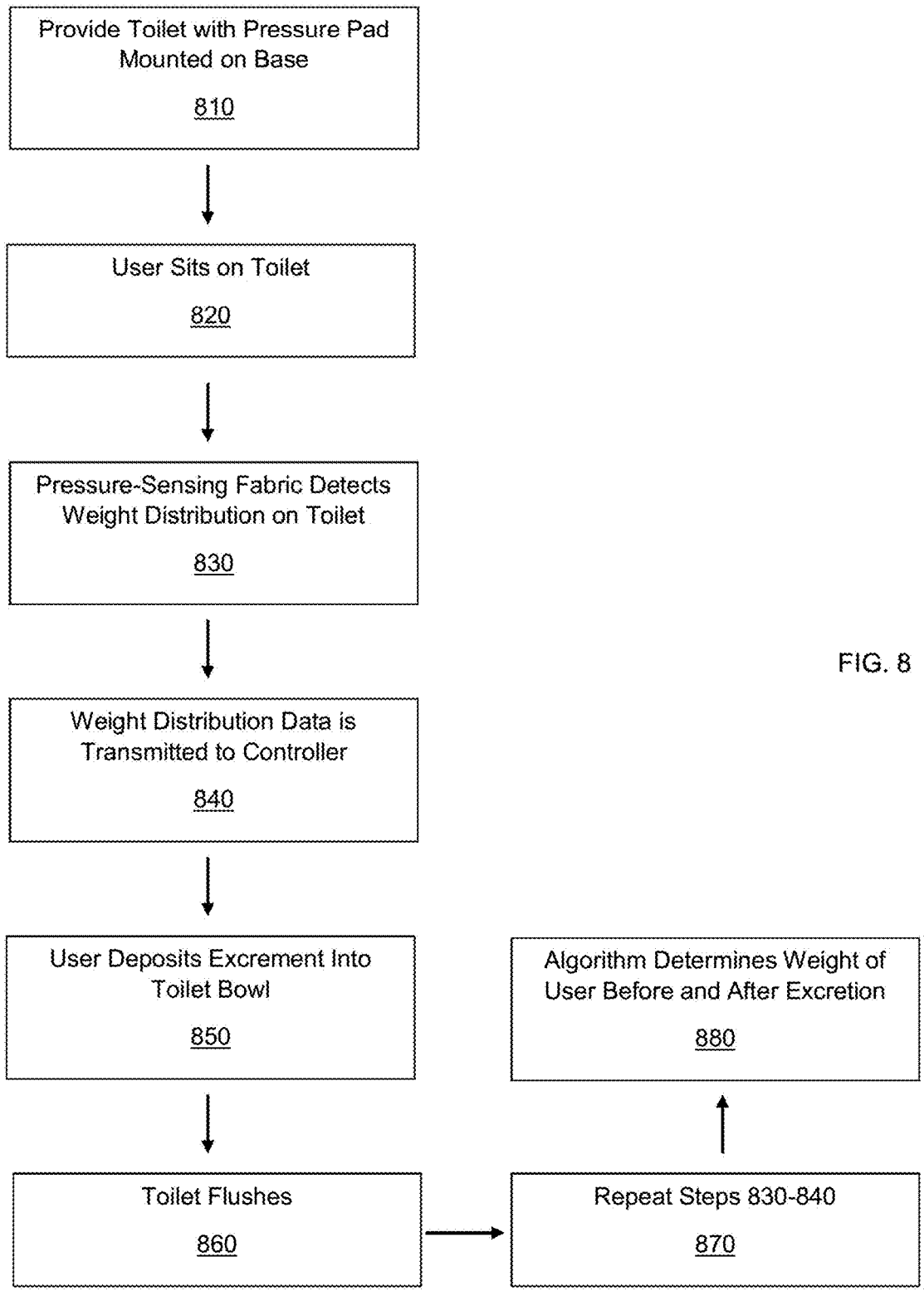
FIG. 8 illustrates a flow chart showing steps which may be taken to determine a user's weight before and after excretion on the toilet according to an embodiment of the disclosure.

FIG. 8 provides a flow chart which shows steps which may be taken to determine a user's weight before and after excretion. In step 810, a toilet is provided which includes a pressure pad placed beneath and around the perimeter of its base as described herein. The user sits on the toilet (step 820) and the pressure-sensing fabric within the pressure pad collects a weight distribution measurement (step 830). This weight distribution data is transmitted to the controller (step 840). The user then excretes bodily waste (urine or feces) into the toilet bowl (step 850) and the toilet flushes (step 760) removing the excrement from the toilet bowl. The pressure-sensing fabric within the pressure pad takes another weight distribution measurement as described in steps 830 and 740 and transmits the data to the controller (step 870). An algorithm stored on the controller calculates the user's weight before and after excretion (step 880).

Figure 9:
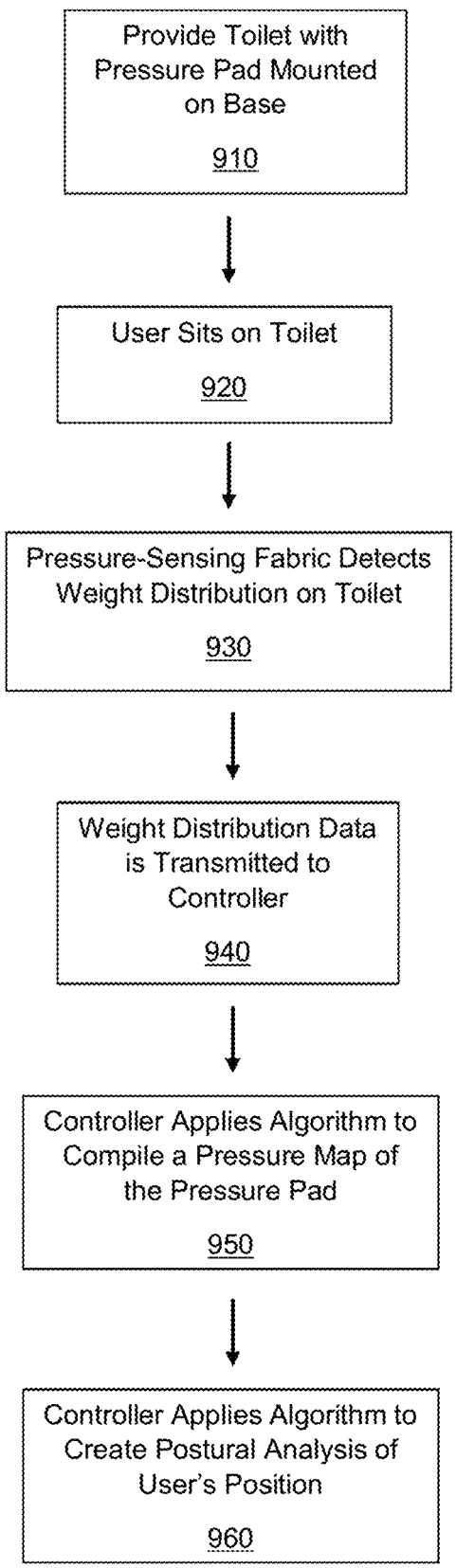
FIG. 9 illustrates a flow chart showing steps which may be taken to evaluate a user's posture according to an embodiment of the disclosure.

FIG. 9 is another flow chart which shows steps which may be taken to assess a user's posture while sitting on the toilet. In step 910, a toilet is provided which includes a pressure pad mounted beneath and around the perimeter of the toilet base as described in embodiments shown herein. The user sits on the toilet (step 920) and the pressure-sensing fabric collects a weight distribution measurement (step 930). This weight distribution data is transmitted to the controller (step 940). An algorithm stored in the controller compiles a pressure map of the weight distribution on the pressure pad (step 950). If the user has an asymmetric posture, the pressure map will show an asymmetric pressure map. The controller then applies an algorithm to the data which creates an assessment of the user's posture (step 960). Such information may be used for diagnostic purposes, for example to diagnose muscular or skeletal pathology. Alternatively, when the toilet is a medical toilet, the information may be used to determine if the user is positioned properly so that another medical device associated with the toilet may be properly operated.

Figure 10:
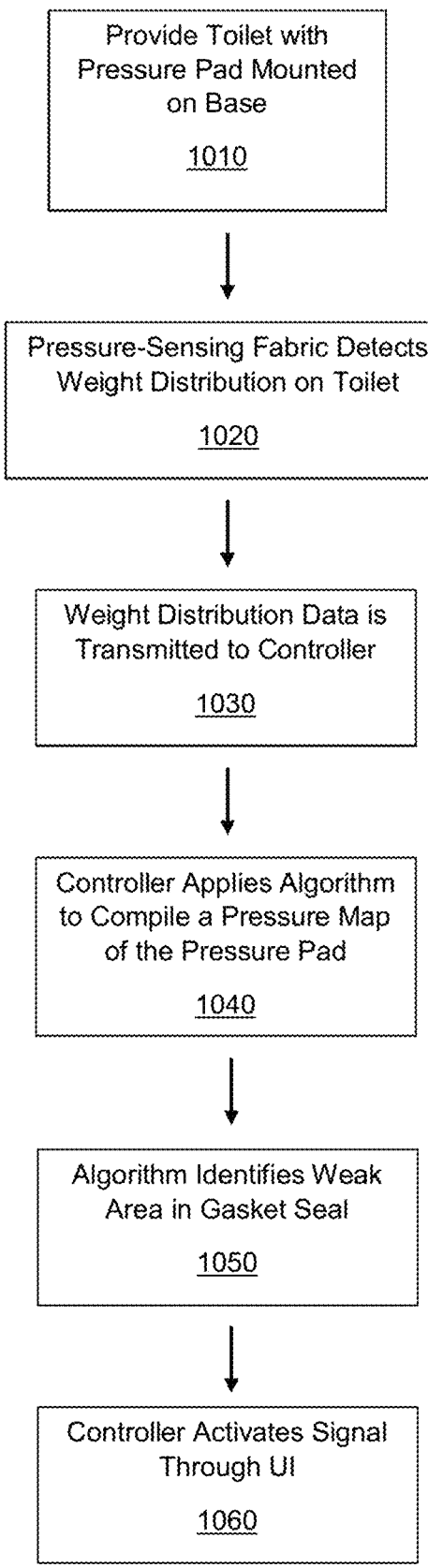
FIG. 10 illustrates a flow chart showing steps which may be taken to evaluate the integrity of the seal of a gasket according to an embodiment of the disclosure.

FIG. 10 is another flow chart which shows steps which may be taken to assess the integrity of the gasket on the toilet. In step 1010, a toilet is provided which includes a pressure pad placed beneath and around the perimeter of its base as described herein. The pressure-sensing fabric within the pressure pad collects a weight distribution measurement (step 1020). This weight distribution data is transmitted to the controller (step 1030). An algorithm stored in the controller compiles a pressure map of the weight distribution on the pressure pad (step 1040). In this example, the pressure map shows an uneven weight distribution which is indicative of a breach in the seal created by the gasket. An algorithm stored on the controller identifies the weak area in the gasket seal (step 1050). In this embodiment, the controller is in electronic connection with a user interface (UI). This UI may be viewed on a user's computer, mobile device, or it may be in the form of a light or screen on the toilet. The controller activates a signal through the UI to alert the user that a section of the gasket is weak and that a water leak is possible (step 1060).

Figure 11:
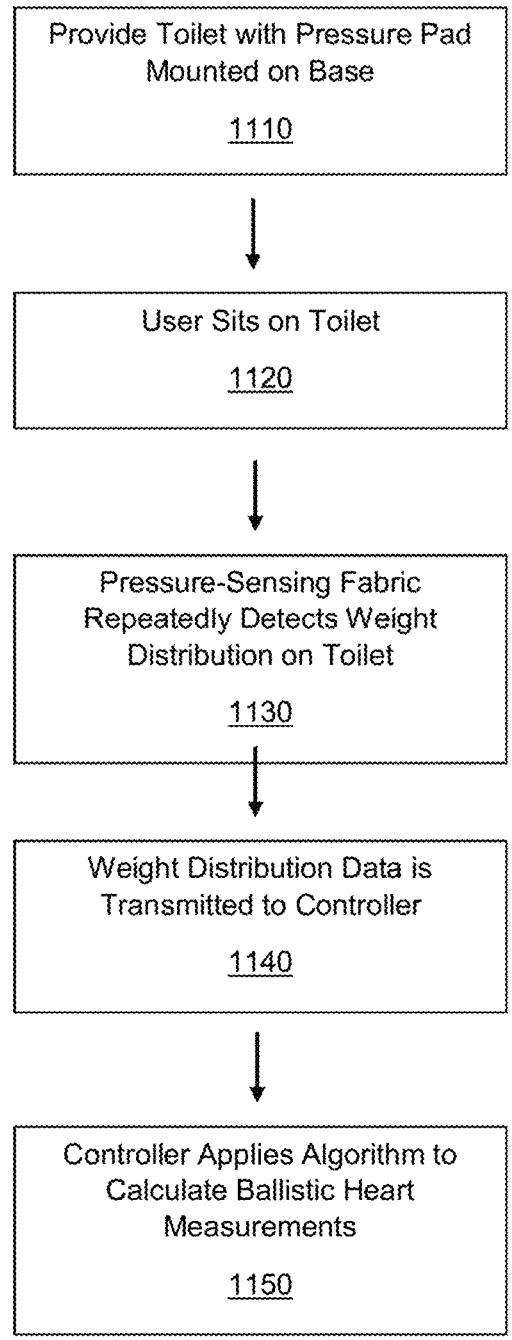
FIG. 11 illustrates a flow chart showing steps which may be taken to collect ballistic heart measurements according to an embodiment of the disclosure.

FIG. 11 is another flow chart which shows steps which may be taken to collect a ballistic heart measurement. In this example, a toilet is provided which includes a pressure pad mounted beneath and around the perimeter of its base as described herein (step 1110). The user sits on the toilet (step 1120) and the pressure-sensing fabric within the pressure pad repeatedly collects weight distribution measurements (step 1130). Each time the user's heart contracts, it ejects a sudden burst of blood into the vessels. The vessels expand and contract causing a change in pressure on the toilet seat. This change in pressure is transmitted to the pressure-sensing fabric within the pressure pad. The weight distribution data is transmitted to the controller (step 1140) which stores an algorithm which analyzes the data to calculate the ballistic heart measurements (step 1150).

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure. Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A pressure pad, comprising:
    a footprint comprising:
        an elliptical or polygonal outline; and
        an orifice within the elliptical or polygonal outline;
    a gasket;
    a controller;
    a first pressure-sensing fabric, wherein the first pressure-sensing fabric is in mechanical communication with the gasket, and in electronic communication with the controller, and comprises:
        a flexible, extensible, and elastic support;
        a plurality of primary tracks comprising extensible and elastic conductive ink or paste which is printed on the support;
        a plurality of secondary tracks comprising extensible and elastic conductive ink or paste which is printed on the support;
        a plurality of piezoresistive ink or paste depositions disposed on the plurality of primary tracks, wherein each of the plurality of piezoresistive ink or paste depositions acts as a pressure-sensing point, wherein each of the plurality of piezoresistive ink or paste depositions is in connection with a secondary track;
        wherein the primary and secondary tracts are in electronic connection with the controller without crossing each other; and
        wherein the controller comprises a memory, and non-transitory computer-readable medium which stores instructions for integrating a plurality of pressure measurements collected by the plurality of pressure-sensing points to compile a distribution of pressure on the pressure pad; and
    wherein the gasket further comprises an inner edge of the gasket which defines an orifice, and which extends further toward a center point of the orifice than the first pressure-sensing fabric, and which houses wires which are in electronic communication with the first pressure-sensing fabric.

2. The pressure pad of claim 1, wherein the gasket comprises a top layer and a bottom layer, wherein both the top layer and the bottom layer comprise a water-resistant, compressible material, and wherein the pressure-sensing fabric is disposed between the top layer and the bottom layer.

3. The pressure pad of claim 1, wherein the inner edge of the gasket comprises a lip surrounding the orifice.

4. The pressure pad of claim 1, wherein the pressure pad comprises a plurality of pressure-sensing zones, wherein each of the plurality of pressure-sensing zones is configured to transmit pressure measurements to the controller independently of each other.

5. The pressure pad of claim 1, wherein the non-transitory computer-readable medium stores instructions for calculating a ballistic heart measurement.

6. The pressure pad of claim 1, wherein the non-transitory computer-readable medium further stores instructions for assessing a posture of a user seated on the toilet.

7. The pressure pad of claim 1, wherein the non-transitory computer-readable medium further stores instructions for identifying a weak region of the gasket based on a reduced distribution of pressure in the weak region.

8. The pressure pad of claim 1, wherein the piezoresistive depositions are adjacent to each other.

9. The pressure pad of claim 1, wherein the piezoresistive depositions overlap each other.

10. The pressure pad of claim 1, wherein the piezoresistive depositions are rectangular in shape.

11. The pressure pad of claim 1, wherein the controller is in electronic connection with an external medical device.

12. The pressure pad of claim 11, wherein the external medical device comprises a medical toilet.

13. A pressure pad, comprising:
    a footprint comprising:
        an elliptical or polygonal outline; and
        an orifice within the elliptical or polygonal outline;
    a gasket;
    a controller;
    a first pressure-sensing fabric, wherein the first pressure-sensing fabric is in mechanical communication with the gasket, and in electronic communication with the controller, and comprises:
        a flexible, extensible, and elastic support;
        a plurality of primary tracks comprising extensible and elastic conductive ink or paste which is printed on the support;
        a plurality of secondary tracks comprising extensible and elastic conductive ink or paste which is printed on the support;
        a plurality of piezoresistive ink or paste depositions disposed on the plurality of primary tracks, wherein each of the plurality of piezoresistive ink or paste depositions acts as a pressure-sensing point, wherein each of the plurality of piezoresistive ink or paste depositions is in connection with a secondary track;
        wherein the primary and secondary tracts are in electronic connection with the controller without crossing each other; and
        wherein the controller comprises a memory, and non-transitory computer-readable medium which stores instructions for integrating a plurality of pressure measurements collected by the plurality of pressure-sensing points to compile a distribution of pressure on the pressure pad;
    a foot pad, comprising:
        an extension of the gasket extending outward from the pressure pad in a direction that is away from a center point of the orifice;
        a second pressure-sensing fabric, wherein the second pressure-sensing fabric is constructed from the same material as the first pressure-sensing fabric, wherein the second pressure-sensing fabric is in mechanical communication with the extension of the gasket, and wherein the wherein the second pressure-sensing fabric is in electronic connection with the controller.

14. The pressure pad of claim 13, wherein the foot pad is adhered to a section of compressible material.

15. The pressure pad of claim 13, wherein the section of compressible material comprises a section of flooring or carpet pad.

16. The pressure pad of claim 13, wherein the foot pad is disposed between and adhered to two sections of compressible material.

17. The pressure pad of claim 16, wherein at least one of the two sections of compressible material comprises a section of flooring or carpet pad.

18. The pressure pad of claim 13, wherein the non-transitory computer-readable medium stores instructions for calculating a combined pressure using the distribution of pressure collected by the first pressure pad and the second pressure pad.

\* \* \* \* \*